US011642552B2

(12) United States Patent
Kamijyo et al.

(10) Patent No.: US 11,642,552 B2
(45) Date of Patent: May 9, 2023

(54) WARMING COMPOSITION AND AEROSOL FORMULATION INCLUDING SAME

(71) Applicants: Toyo Aerosol Industry Co., Ltd., Tokyo (JP); THE UNIVERSITY OF TOKYO, Tokyo (JP)

(72) Inventors: Hokuto Kamijyo, Tokyo (JP); Yasutomo Nakajima, Tokyo (JP); Toru Wakihara, Tokyo (JP); Yasuo Yonezawa, Tokyo (JP)

(73) Assignees: Toyo Aerosol Industry Co., Ltd., Tokyo (JP); The University of Tokyo, Tokyo (JP)

(*) Notice: Subject to any disclaimer, the term of this patent is extended or adjusted under 35 U.S.C. 154(b) by 823 days.

(21) Appl. No.: 16/570,743

(22) Filed: Sep. 13, 2019

(65) Prior Publication Data

US 2020/0009066 A1 Jan. 9, 2020

Related U.S. Application Data

(63) Continuation of application No. PCT/JP2017/019071, filed on May 22, 2017.

(30) Foreign Application Priority Data

Mar. 17, 2017 (WO) .................. PCT/JP2017/010981

(51) Int. Cl.
| | |
|---|---|
| A61Q 19/00 | (2006.01) |
| B65D 83/66 | (2006.01) |
| B65D 83/68 | (2006.01) |
| A61K 8/04 | (2006.01) |
| A61K 8/34 | (2006.01) |
| A61K 8/26 | (2006.01) |
| A61K 8/25 | (2006.01) |

(52) U.S. Cl.
CPC .............. *A61Q 19/00* (2013.01); *A61K 8/046* (2013.01); *A61K 8/25* (2013.01); *A61K 8/26* (2013.01); *A61K 8/345* (2013.01); *B65D 83/66* (2013.01); *B65D 83/682* (2013.01); *A61K 2800/242* (2013.01); *A61K 2800/413* (2013.01)

(58) Field of Classification Search
CPC ....... A61K 2800/413; A61K 8/25; A61K 8/26
See application file for complete search history.

(56) References Cited

U.S. PATENT DOCUMENTS

| | | | |
|---|---|---|---|
| 3,250,680 A | 5/1966 | Menkart et al. | |
| 6,196,275 B1* | 3/2001 | Yazawa | B65B 31/003 141/3 |
| 7,632,771 B2 | 12/2009 | Iacopi et al. | |
| 2003/0183651 A1* | 10/2003 | Greer, Jr. | B65D 83/36 222/402.1 |
| 2006/0018968 A1* | 1/2006 | Melbouci | D21H 19/54 424/701 |
| 2008/0128426 A1* | 6/2008 | Rick | A61K 8/26 424/684 |
| 2011/0217358 A1* | 9/2011 | Feleki | A61K 9/14 424/681 |
| 2012/0132563 A1 | 5/2012 | Tov et al. | |
| 2012/0171418 A1 | 7/2012 | Lin et al. | |
| 2013/0078191 A1 | 3/2013 | Teramoto et al. | |
| 2015/0118314 A1 | 4/2015 | Feleki et al. | |
| 2015/0232260 A1 | 8/2015 | Dann et al. | |
| 2016/0215171 A1 | 7/2016 | Marcellan et al. | |
| 2017/0367461 A1* | 12/2017 | Tsubouchi | A61K 8/345 |

FOREIGN PATENT DOCUMENTS

| | | | |
|---|---|---|---|
| EP | 187912 A2 | 7/1986 | |
| EP | 2149375 A1 | 2/2010 | |
| JP | H04-86424 A | 3/1992 | |
| JP | H04-89424 A | 3/1992 | |
| JP | H10-306276 A | 11/1998 | |
| JP | 2000-007520 A | 1/2000 | |
| JP | 2000-212051 A | 8/2000 | |
| JP | 2004-224706 A | 8/2004 | |
| JP | 2007/015934 A | 1/2007 | |
| JP | 2009/209089 A | 9/2009 | |
| JP | 2011-225522 A | 11/2011 | |
| JP | 2011-529098 | 12/2011 | |
| JP | 2012-017464 A | 1/2012 | |
| JP | 2012017464 A * | 1/2012 | ............. A01N 25/06 |
| JP | 2013-035783 A | 2/2013 | |
| JP | 2016-530035 A | 9/2016 | |

(Continued)

OTHER PUBLICATIONS

Crangle, Jr (2018 Minerals Yearbook Zeolites, USGS, 2021, 84.1-84.4) (Year: 2021).*
Valtchev et al (Langmuir, 2005, vol. 21, pp. 10724-10729) (Year: 2005).*
JP-2012017464-A (Espacenet English translation, downloaded Jun. 2022) (Year: 2022).*
International Preliminary Report on Patentability and Written Opinion in International Application No. PCT/JP2017/019071 dated Sep. 26, 2019, 12 pages.
International Preliminary Report on Patentability and Written Opinion in International Application No. PCT/JP2017/010981 dated Sep. 26, 2019, 10 pages.

(Continued)

*Primary Examiner* — Mark V Stevens
(74) *Attorney, Agent, or Firm* — Marshall, Gerstein & Borun LLP

(57) ABSTRACT

The present invention aims to provide a warming composition showing a favorable dispersion stability after long-term storage, a high warming impact, and improvement of zeolite-specific deterioration of feeling of use, and to provide an aerosol formulation containing the warming composition. This object is achieved with a warming composition containing zeolite nanoparticles having an average particle size of not more than 500 nm, wherein the temperature of the composition is rapidly increased by heat generated by hydration reaction between the zeolite and water.

11 Claims, 6 Drawing Sheets

(56) References Cited

FOREIGN PATENT DOCUMENTS

| JP | 2017-506609 A | 3/2017 | | |
|---|---|---|---|---|
| WO | WO-86/05389 A1 | 9/1986 | | |
| WO | WO-2016/121087 A1 | 8/2016 | | |
| WO | WO-2016/121851 A1 | 8/2016 | | |
| WO | WO-2016121087 A1 * | 8/2016 | ............. | A45D 34/04 |

OTHER PUBLICATIONS

Database WPI, Week 199218, Thomson Scientific, London, GB, AN 1992-147540, 2 pages.
Extended European Search Report in EP Application No. 17900393.4 dated Feb. 24, 2020, 12 pages.
Search Report in International Application No. PCT/JP2017/019071 dated Aug. 8, 2017, 4 pages.

* cited by examiner

After being left to stand for a period corresponding to one year

After being left to stand for a period corresponding to two years

After being left to stand for a period corresponding to three years

WARMING COMPOSITION AND AEROSOL FORMULATION INCLUDING SAME

CROSS-REFERENCE TO RELATED APPLICATION

This is a continuation of International Application No. PCT/JP2017/019071, filed on May 22, 2017, and designated the U.S., and claims priority from International Application No. PCT/JP2017/010981 which was filed on Mar. 17, 2017, the entire contents of which are incorporated herein by reference.

TECHNICAL FIELD

The present invention relates to a warming composition containing a heat-generating substance, and an aerosol formulation containing it.

BACKGROUND ART

By giving a heat-generating property to a composition for application to the skin of a human body, production of a variety of effects called the thermal effect can be expected. Examples of such effects include pleasant feeling during the application caused by warmth, activation of the skin by promotion of blood circulation (recovery from fatigue, activation of metabolism, improvement of aesthetic appearance, and the like), and improvement of the removal performance for epidermal debris by expansion of pores and heat.

As heat-generating formulations that produce such effects, compositions containing zeolite or a polyhydric alcohol, which compositions generate heat when they are applied to the skin and allowed to react with water in the skin, have been developed (see, for example, Patent Documents 1 to 3). These formulations are stored mainly in a state where they are filled in tubes and the like, and in some cases, zeolite or polyhydric alcohol adsorbs moisture in the air when, for example, a cap is opened. Thus, they have problems in the storage stability. Moreover, since the amount of water present in the skin is limited, the formulations have only low warming impacts.

Regarding these problems, it is known that the storage stability can be improved by including a heat-generating composition in an aerosol container having a high sealing performance. For example, Patent Document 4 uses an aerosol container in which a propellant-filling space and two stock solution-filling spaces are formed. By using such an aerosol container, the sealing performance can be improved, and, in addition, by separately providing a space to be filled with a heat-generating substance and a space to be filled with water, and mixing the substance with water by spraying, the warming impact can be improved.

PRIOR ART DOCUMENTS

Patent Documents

Patent Document 1: JP-A-H4-89424
Patent Document 2: EP 187912
Patent Document 3: U.S. Pat. No. 3,250,680
Patent Document 4: WO 2016/121087

SUMMARY OF THE INVENTION

The present inventors inferred that a composition containing zeolite may exhibit zeolite-specific deterioration of feeling of use (rough feeling) compared to compositions using only polyhydric alcohol as a heat-generating component. Further, there has been a problem in the dispersion stability since long-term storage of a container filled with the composition causes precipitation of zeolite, which is a powder (first problem).

Further, as a result of study on use of a warming composition as an aerosol formulation, the present inventors found a problem with the aerosol formulation concerning the discharge mechanism for spraying of the composition using a propellant. Since zeolite is a powder, an aerosol formulation using zeolite causes clogging of the discharge mechanism (second problem).

The present invention solves these problems.

In order to solve these problems, the present inventors intensively studied to discover that the problems can be solved by using nano-sized zeolite instead of micron-sized zeolite, which has been conventionally used.

The first point of the present invention is a warming composition comprising at least zeolite nanoparticles having an average particle size of not more than 500 nm.

The warming composition preferably further contains a polyhydric alcohol.

The second point of the present invention is
an aerosol formulation comprising: a first container containing a first composition containing a composition containing at least zeolite nanoparticles having an average particle size of not more than 500 nm; and a second container containing a second composition containing at least water; the first container and the second container being contained in a discharge container provided with a discharge mechanism, wherein a space formed between the discharge container and the first container and the second container is filled with a propellant.

The first composition preferably further contains a polyhydric alcohol. Preferably, the first container containing the first composition containing the first composition is contained in a discharge container provided with a discharge mechanism; a space formed between the first container and a partition wall of the discharge container in the discharge container is filled with a propellant; and a filling in the first container and a filling in the second container are simultaneously discharged.

The third point of the present invention is
an aerosol formulation comprising a first container containing a first composition containing a composition containing at least zeolite nanoparticles having an average particle size of not more than 500 nm, the first container being contained in a discharge container provided with a discharge mechanism, wherein a space formed between the first container and a partition wall of the discharge container in the discharge container is filled with a propellant.

The first composition preferably further contains a polyhydric alcohol.

The fourth point of the present invention is
an aerosol formulation comprising: a first container filled with a first composition containing at least zeolite nanoparticles having an average particle size of not more than 500 nm; and a second container filled with a second composition containing at least water; the first container and the second container being contained in a discharge container provided with a discharge mechanism, wherein a space formed between the discharge container and the first container and the second container is filled with a propellant,
wherein the first composition and the second composition contact each other to generate heat when the compositions are discharged by the propellant.

The first composition preferably further contains a polyhydric alcohol.

The present invention can provide a warming composition showing a favorable dispersion stability after long-term storage, a high warming impact, and improvement of zeolite-specific deterioration of feeling of use.

Further, the aerosol formulation of the present invention can prevent clogging of the discharge mechanism and an increase in the reaction of water in the air with the zeolite in the warming composition during storage. Further, by filling the warming composition and the composition containing water into separate spaces in an aerosol container, and mixing these compositions by spraying, the warming impact can be improved independently of the amount of water present in the skin.

MODE FOR CARRYING OUT THE INVENTION

Figure 1:
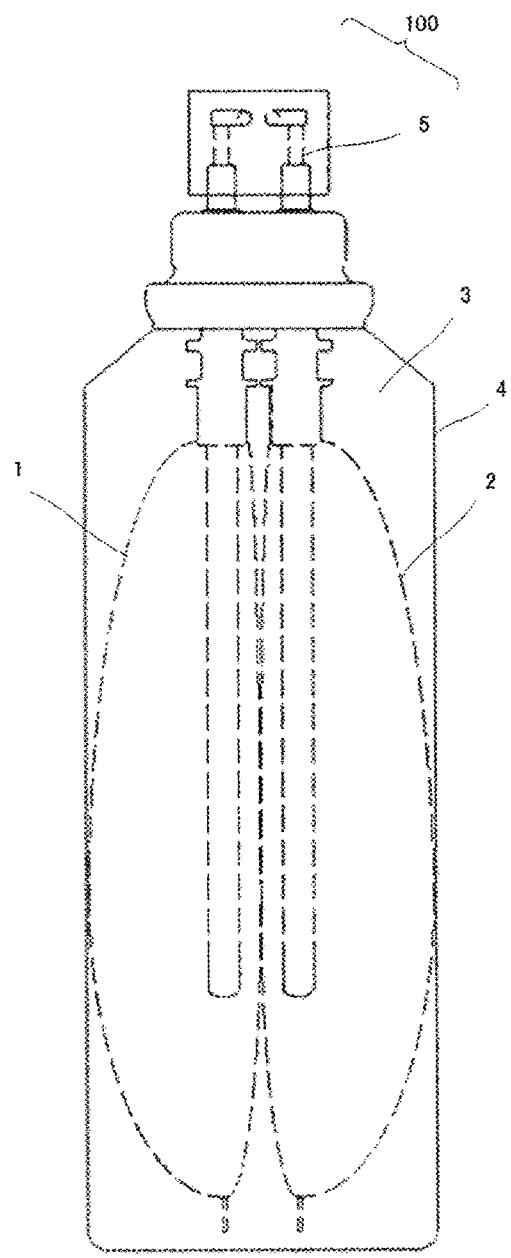
FIG. 1 is a front schematic view of an aerosol formulation according to one embodiment of the present invention.

The present invention is described below by way of embodiments. However, the present invention is not limited to particular embodiments.

The first embodiment of the present invention is a warming composition, and the composition comprises at least zeolite nanoparticles having an average particle size of not more than 500 nm.

The "warming composition" used in the present invention is a composition that generates heat by reaction with water. It generates heat, for example, when it is discharged onto a palm of a human body and reacts with water on the palm, or when it is allowed to react with water (an aqueous solution) provided separately.

The zeolite nanoparticles used in the present invention have an average particle size of not more than 500 nm, and generate heat of hydration when they are mixed with water. The lower limit of the average particle size is not limited, and the average particle size is preferably not less than 5 nm, more preferably not less than 10 nm, still more preferably not less than 20 nm, still more preferably not less than 25 nm. Regarding the upper limit, the average particle size is preferably not more than 400 nm, more preferably not more than 300 nm, still more preferably not more than 200 nm, still more preferably not more than 150 nm.

As described later in detail, the average particle size is the value of the number average particle size measured with a scanning electron microscope.

Examples of the zeolite used in the warming composition of the present invention include those with a $SiO_2/Al_2O_3$ ratio of not more than 40, preferably not more than 20, more preferably not more than 6 among the frameworks registered in International Zeolite Association.

Among these, preferred examples of the zeolite used in the present invention include type A zeolite nanoparticles such as type 3A synthetic zeolite (1-x)$Na_2O \cdot xK_2O \cdot Al_2O_3 \cdot 2SiO_2$ (x≤0.95), type 4A synthetic zeolite $Na_2O \cdot Al_2O_3 \cdot 2SiO_2$, and type 5A synthetic zeolite (1-x)$Na_2O \cdot 0.5xCaO \cdot Al_2O_3 \cdot 2SiO_2$ (x≤0.95).

The content of the zeolite nanoparticles is usually 1 to 70% by mass with respect to 100% by mass of the warming composition. Regarding the lower limit, the content is preferably not less than 3% by mass, more preferably not less than 5% by mass. Regarding the upper limit, the content is preferably not more than 60% by mass, more preferably not more than 50% by mass.

In cases where the content of the zeolite is within the range described above, a sufficient warming action of the warming composition can be obtained while the temperature does not become high enough to cause burns on the skin. Further, the warming composition can have an appropriate viscosity when it is discharged from the aerosol container.

The warming composition preferably contains a polyhydric alcohol. A polyhydric alcohol reacts with water to generate heat, and can be a major component of a liquid medium for zeolite.

Specific examples of the polyhydric alcohol used for the warming composition include propylene glycol (PG), 1,3-butylene glycol (BG), polyethylene glycol (PEG), glycerin, and polyglycerin, which are in a liquid form at normal temperature (at a temperature of 20° C.). One of these may be used alone, or two or more of these may be used in combination.

Among these, polyethylene glycol is preferred since a sufficient warming action can be obtained for the warming composition. The polyethylene glycol preferably contains molecules having an average molecular weight of not more than 1000, but molecules having an average molecular weight of more than 1000 may be used in combination therewith.

The content of the polyhydric alcohol is usually 30 to 99% by mass with respect to 100% by mass of the warming composition. Regarding the lower limit, the content is preferably not less than 40% by mass, more preferably not less than 50% by mass. Regarding the upper limit, the content is preferably not more than 97% by mass, more preferably not more than 95% by mass.

The warming composition may contain a thickener or a dispersant for stable dispersion of the zeolite nanoparticles in the warming composition.

Preferred examples of the thickener or the dispersant include natural polymers, synthetic polymers, surfactants, and fine inorganic particles (inorganic substances and lamellar compounds which are formed into fine particles). Their particular examples of the thickener or the dispersant include xanthan gum, carbomer, nonionic surfactants, and fumed silica. One of these may be used alone, or two or more of these may be used in combination. The thickener may be either hydrophilic or hydrophobic.

The content of the thickener or the dispersant is usually 0.01 to 20% by mass with respect to 100% by mass of the warming composition. Regarding the lower limit, the content is preferably not less than 0.1% by mass, more preferably not less than 0.5% by mass. Regarding the upper limit, the content is preferably not more than 15% by mass, more preferably not more than 10% by mass.

The viscosity of the warming composition after preparation is usually 1 to 100,000 mPa·s in terms of the value obtained by measuring a sample at 20° C. using a B-type viscometer. Regarding the lower limit, the viscosity is preferably not less than 100 mPa·s, more preferably not less than 1000 mPa·s. Regarding the upper limit, the viscosity is preferably not more than 70,000 mPa·s, more preferably not more than 50,000 mPa·s.

In cases where a polyethylene glycol is used as the polyhydric alcohol, fumed silica is preferably used as the thickener. The fumed silica may be either hydrophilic or hydrophobic.

The method of preparing the warming composition is not limited, and the composition may be prepared according to a conventional method. More specifically, the polyhydric alcohol, thickener, and/or the like are fed into a melting pot at the above-described ratios, and then uniformly melted by heating, to form a gel. Thereafter, granules containing zeolite nanoparticles as a major component are fed thereto, and mixed and dispersed such that the component phase is homogenized, to provide a composition.

In general, the composition filled in an aerosol formulation preferably has an appropriate viscosity for obtaining a desired discharge amount and for maintaining a favorable dispersibility for a long period in a composition containing a powder. The present inventors discovered a new problem that it is very difficult to increase the viscosity of polyethylene glycol, which is preferably used in the present invention. As a result of intensive study to solve this problem, the present inventors discovered that fumed silica is a thickener that can sufficiently increase the viscosity of polyethylene glycol. The discovery that a sufficient improvement in the viscosity can be achieved by combination of fumed silica with polyethylene glycol is thought to be applicable not only to the warming composition of the present invention, but also to a wide variety of compositions containing polyethylene glycol.

Thus, another embodiment of the present invention is a method of increasing the viscosity of a polyethylene glycol-containing composition, the method comprising a step of adding fumed silica.

In this embodiment, the PEG content in the composition is usually not less than 10% by mass, preferably not less than 30% by mass, more preferably not less than 50% by mass.

The fumed silica used in the present embodiment has an average particle size of usually 5 to 50 nm, preferably 10 to 30 nm. The average particle size is a value measured using a transmission electron microscope.

An example of the fumed silica which satisfies these physical properties is AEROSIL (registered trademark) 200 (manufactured by Nippon Aerosil Co., Ltd.), which is commercially available.

In another embodiment of the aerosol formulation, a first composition as a warming composition and/or a second composition containing at least water is/are filled in a discharge container. For giving an appropriate viscosity to the composition(s) to be filled, the second composition containing at least water may further contain an ester, a thickener such as a water-soluble polymer, and/or the like.

The ester acts as a humectant or a feeling-of-use-improving agent such as an emollient, especially in cases of application to a human body.

Examples of the ester include higher fatty acid esters such as ethyl linoleate, isopropyl myristate, isopropyl palmitate, isopropyl isostearate, isopropyl lanolin fatty acid, hexyl lanolate, myristyl myristate, cetyl lactate, octyldodecyl myristate, decyl oleate, octyldodecyl oleate, cetyl octanoate, dioctyl succinate, glyceryl tricaprylate, glyceryl triisostearate, propylene glycol dicaprylate, ethyl oleate, cetyl palmitate, and glyceryl tri(caprylate/caprate). One of these may be used alone, or two or more of these may be used in combination.

Examples of the water-soluble polymer include natural polymers such as guar gum, carrageenan, xanthan gum, dextran, hyaluronic acid, gelatin, casein, albumin, collagen, and alginate; and synthetic polymers such as polyvinyl alcohol, polyvinyl pyrrolidone, carboxyvinyl polymers, (meth)acrylate-based polymers, and cellulose-based polymers. One of these may be used alone, or two or more of these may be used in combination.

The content of the thickener in the second composition is usually 0.01 to 10% by mass, preferably 0.05 to 5% by mass, more preferably 0.1 to 3% by mass with respect to 100% by mass of the second composition.

When the content of the thickener in the second composition is within this range, there is no feeling of stickiness, and a favorable feeling of use can be obtained, especially in cases of application to a human body.

The second composition contains at least water. In addition, the second composition may contain an alcohol such as ethanol, n-propanol, isopropanol, or butanol.

In another embodiment, for the purpose of, for example, moisturizing the skin, one or both of the first composition and the second composition may contain an oily component.

Examples of the oily component include fats and oils such as olive oil, soy oil, sesame oil, rapeseed oil, avocado oil, and castor oil; waxes such as beeswax, carnauba wax, and jojoba oil; higher alcohols such as cetyl alcohol, stearyl alcohol, oleyl alcohol, behenyl alcohol, lauryl alcohol, and myristyl alcohol; hydrocarbons such as paraffin, polyisobutene, squalane, and vaseline; higher fatty acids such as lauric acid, myristic acid, palmitic acid, stearic acid, and oleic acid; esters such as isopropyl adipate, isopropyl myristate, stearyl stearate, and isopropyl palmitate; silicones such as dimethylpolysiloxane, methylphenylpolysiloxane, polyether-modified polysiloxane, and alkyl-modified polysiloxane; and polyhydric alcohols such as ethylene glycol and glycerin.

Further, when necessary, one or both of the first composition and the second composition may contain an antiseptic, stabilizer, pH adjusting agent, antioxidant, chelating agent, excipient, perfume, UV inhibitor, humectant, surfactant, another heat-generating substance (such as a capsicum extract or magnesium sulfate), or the like.

In the present embodiment, the dosage forms of the first composition and the second composition are not limited. In cases of use as a cosmetic, each composition is preferably a gel formulation or a cream formulation from the viewpoint of production of their effects. The first composition and the second composition may be emulsified with a known surfactant(s), if necessary.

As the container to be filled with the warming composition, a known container may be used. Specific examples of the container include tubes, pumps, and aerosol containers.

FIG. 1 is a front schematic view of the aerosol formulation according to the second or fourth embodiment. In an aerosol formulation 100, a first container 1 and a second container 2 are contained and sealed in a discharge container having a housing 4 and a discharge mechanism 5. The first container 1 is filled with a first composition containing at least zeolite nanoparticles, and the second container 2 is filled with a second composition containing at least water. In the discharge container, a space 3 is formed between the housing 4 and the first container 1 and the second container 2, and the space 3 is filled with a propellant for discharging the first composition and the second composition from the discharge mechanism 5. The discharge mechanism 5 includes discharge outlets for discharging each of the compositions filled in the first container 1 and the second container 2. When the first composition and the second composition discharged from the discharge outlets contact each other, a warming composition generating heat can be formed.

Figure 2:
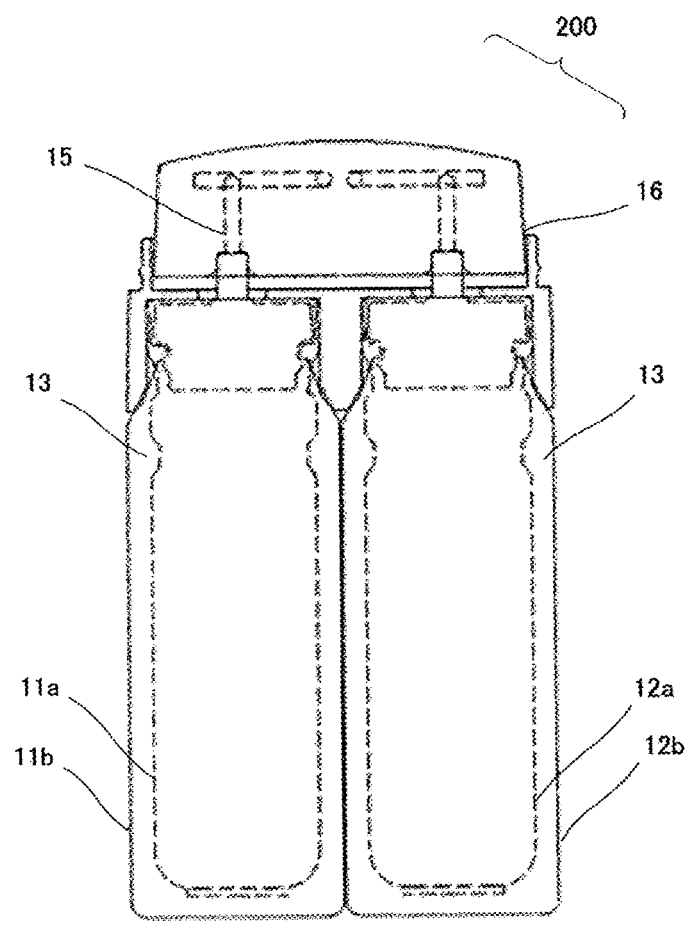
FIG. 2 is a front schematic view of an aerosol formulation according to one embodiment of the present invention.

FIG. 2 is a front schematic view of the aerosol formulation according to the second or fourth embodiment. An aerosol formulation 200 comprises: an aerosol set containing a first outer container 11b; a second outer container 12b; and a cap 16 provided with a discharge mechanism 15. The first outer container 11b contains a first inner container 11a, and the first inner container 11a is filled with a first composition containing at least zeolite nanoparticles having an average particle size of not more than 500 nm. The second outer container 12b contains a second inner container 12a, and the second inner container 12a is filled with a second composition containing at least water. In the aerosol set, a space 13 is formed between the first outer container 11b and the first inner container 11a, and between the second outer container 12b and the second inner container 12a. The space is filled with a propellant for discharging the first composition and the second composition from the discharge mechanism 15. The discharge mechanism 15 includes discharge outlets for discharging each of the compositions filled in the first inner container 11a and the second inner container 12a. When the first composition and the second composition discharged from the discharge outlets contact each other, a warming composition can be formed. The first outer container and the second outer container may be detachable from the cap. In cases where the first outer container and/or the second outer container is/are detachable from the cap, when the remaining amount of the composition in the container contained in one of the outer containers is small, it can be replaced.

Figure 3:
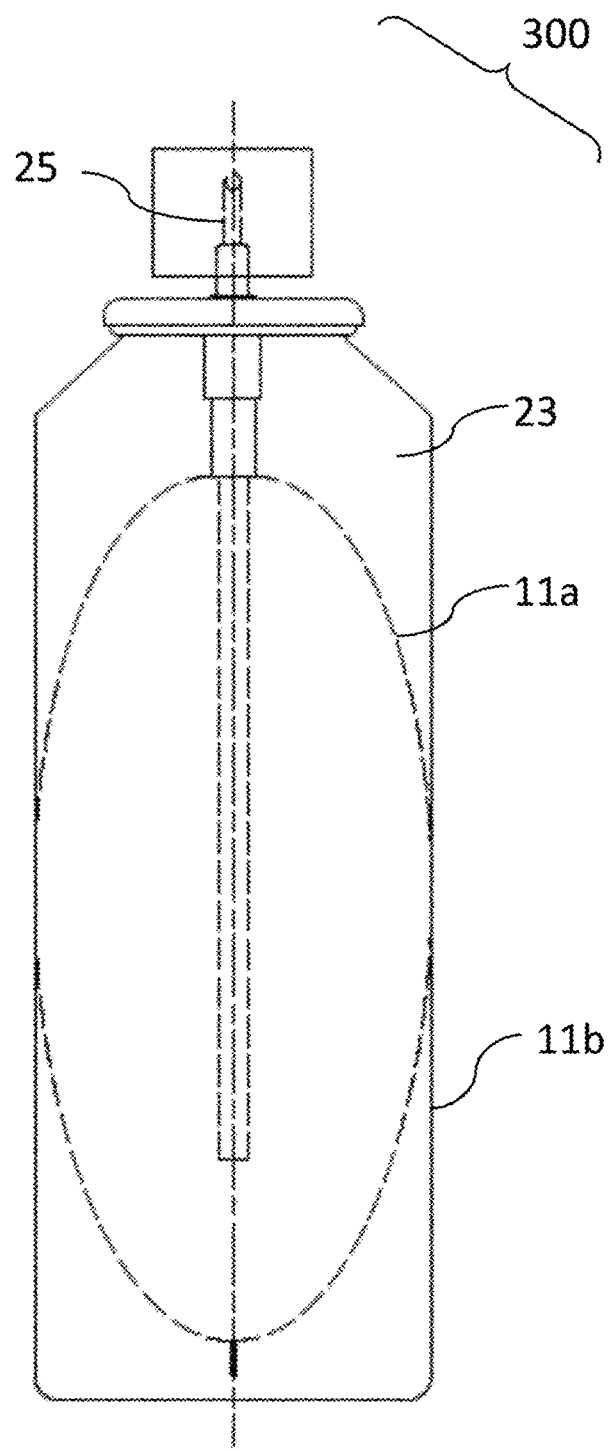
FIG. 3 is a front schematic view of an aerosol formulation according to one embodiment of the present invention.

FIG. 3 is a front schematic view of the aerosol formulation according to the third embodiment. In an aerosol formulation 300, a first inner container 11a as a collapsible flexible bag is sealed at an opening section in the lower side of a discharge mechanism 25, and restricts or prevents mixing of a first composition containing at least zeolite nanoparticles having an average particle size of not more than 500 nm filled in the first inner container with water present outside the first inner container 11a. Between a first outer container 11b and the first inner container 11a, a space 23 is formed, and the space is filled with a propellant for discharging the first composition from a discharge mechanism 25. The discharge mechanism 25 includes a discharge outlet for discharging the composition filled in the first inner container 11a, and a channel to the outside of the bag is formed when a valve operates. By pressure from a propellant arranged between the first inner container 11a and the first outer container 11b, pressurization of the first inner container 11a occurs to cause discharge of the first composition filled therein to the outside of the first outer container 11b. When the discharged first composition contacts water present in the air or on the skin of a human body, a warming composition can be formed. The present embodiment is generally called "bag on valve" or "bag in can", and can be used for, for example, dispensing a gel composition. An aerosol formulation using a "bag on valve" can discharge the content of the bag similarly at any angle, and 99% of the content of can be discharged.

The propellant filled in the discharge container or the aerosol container is not limited, and may be a liquefied gas or a compressed gas. The aerosol formulation according to the present embodiment is a formulation in which the first composition and the second composition are discharged from a discharge container or an aerosol container to allow the compositions to contact each other, thereby generating heat. Therefore, the compositions do not necessarily need to be mixed together after the discharge. Although a flammable liquefied gas such as a liquefied petroleum gas or dimethyl ether may be used as the propellant, it is preferred to use a safe compressed gas.

The compressed gas is not limited, however, from the viewpoint of the safety as described above, a non-flammable gas is preferably used. Specific examples of the non-flammable gas include carbon dioxide, nitrogen, and nitrous oxide.

In the present embodiment, the discharge mechanism is not limited. The discharge mechanism preferably has a structure with which desired amounts of the first composition and the second composition can be discharged at the same time. Further, the discharge outlet of the discharge mechanism may be covered with a net or the like so that the water contained in the second composition can be sufficiently mixed with the zeolite nanoparticles when the second composition is brought into contact with the first composition.

Such an aerosol product for formation of a warming cream composition in the present invention can be applied to a variety of uses. In particular, since a very good warming action is produced when it is applied to a human body, it can be suitably used for human bodies.

More specifically, the aerosol product can be used as a cosmetic such as a cosmetic cream, pack material, or foundation; or a personal care product such as a shaving cream or facial cleanser.

EXAMPLES

The present invention is described below in more detail by way of Examples and Comparative Examples. However, the present invention is not restricted by these. The parts and % used in the Examples and Comparative Examples are expressed on a mass basis unless otherwise specified.

<Method of Measuring Average Particle Sizes of Zeolite Nanoparticles and Fumed Silica>

Regarding zeolite nanoparticles, observation of each sample was carried out using a field-emission electron microscope (apparatus name: FE-SEM, JSM-7000F, manufactured by JEOL). The horizontal Feret diameter was measured for not less than 30 primary particles randomly measured, and their arithmetic average was provided as the average particle size. Regarding fumed silica, measurement was carried out in the same manner using a transmission electron microscope.

<Temporal Stability Test for Dispersibility of Warming Composition>

Components were mixed at the contents (%) shown in Table 1 to produce Examples 1 to 4 and Comparative Examples 1 and 2 as warming gels.

TABLE 1

| | Example 1 | Example 2 | Example 3 | Example 4 | Comparative Example 1 | Comparative Example 2 |
|---|---|---|---|---|---|---|
| Zeolite nanoparticles (50 nm) | 13 | 23.1 | — | — | — | — |
| Zeolite nanoparticles (300 nm) | — | — | 13 | 23.1 | — | — |
| Zeolite micron particles (15 μm) | — | — | — | — | 13 | 23.1 |
| PEG-400 | 78.3 | 69.2 | 78.3 | 69.2 | 78.3 | 69.2 |
| AEROSIL 200 | 8.7 | 7.7 | 8.7 | 7.7 | 8.7 | 7.7 |
| After being left to stand for 1 year | ○ | ◉ | ○ | ○ | X | X |
| After being left to stand for 2 years | Δ | ◉ | Δ | ○ | X | X |
| After being left to stand for 3 years | Δ | ○ | Δ | ○ | X | X |

Figure 4:
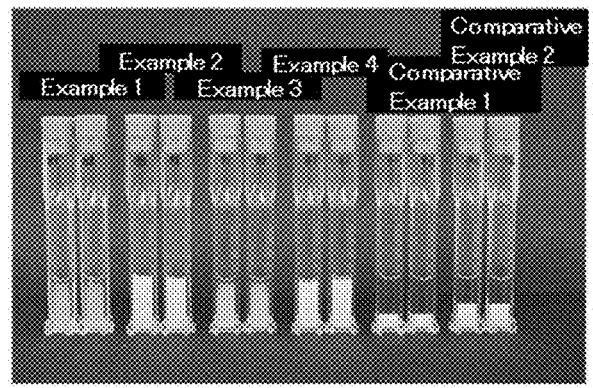
FIG. 4 is a photograph showing dispersion stability of a warming composition according to one embodiment of the present invention (drawing-substituting photograph).
Figure 4:
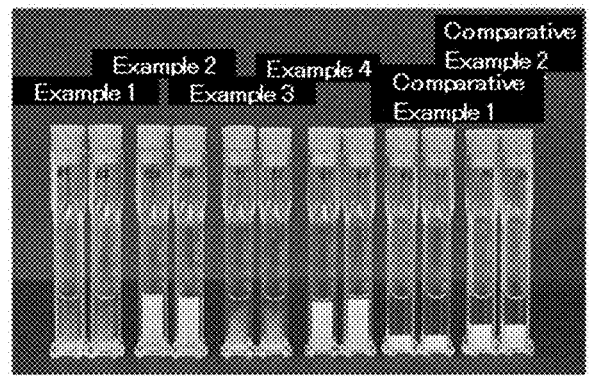
Figure 4:
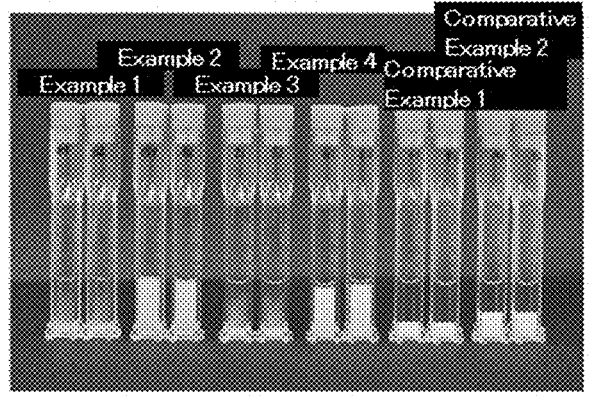

Using a particle size distribution/dispersion stability analyzer LUMiSizer/Fuge, Examples 1 to 4 and Comparative Examples 1 and 2 were subjected to accelerated precipitation by the centrifugal force, and predictive analysis of the degrees of precipitation over time was carried out. The degrees of precipitation were as shown in FIG. 4. Evaluation was carried out visually according to the following standard. The results are shown in Table 1.

◉: No precipitation at all

○: Slight precipitation

Δ: Moderate precipitation x: Complete precipitation

The warming compositions containing zeolite micron particles (Comparative Examples 1 and 2) completely precipitated in one year, but the warming compositions containing 23.1% by mass zeolite nanoparticles (Examples 2 and 4) hardly showed precipitation even after being left to stand for a period corresponding to three years. It was also found that the dispersion stability of the warming composition increases as the average particle size of the zeolite nanoparticles decreases, and as the content of the zeolite nanoparticles increases.

<Test for Increasing Viscosity of Liquid Medium Mainly Containing Polyethylene Glycol>

Instead of AEROSIL 200, which was used in Example 1, the thickeners shown below in Table 2 were used to prepare warming compositions. As a result, none of the thickeners could be dissolved in polyethylene glycol, and no increase in the viscosity of the liquid medium was found.

TABLE 2

| Product name | Component name | Result | Type |
|---|---|---|---|
| Cabopol 940 | Carbomer | x | Aqueous thickener |
| Cabopol 980 | Carbomer | x | |
| Cabopol Ultrez 10 | Carbomer | x | |
| Cabopol 941 | Carbomer | x | |
| Cabopol 981 | Carbomer | x | |
| Cabopol Ultrez 21 | (Acrylates/alkyl acrylate (C10-30)) crosspolymer | x | |
| Cabopol Ultrez 20 | (Acrylates/alkyl acrylate (C10-30)) crosspolymer | x | |
| Cabopol Ultrez 30 | Carbomer | x | |
| Pemulen TR-2 | (Acrylates/alkyl acrylate (C10-30)) crosspolymer | x | |
| Aristoflex HMB | (Ammonium acryloyldimethyltaurate beheneth-25 methacrylate) crosspolymer | x | |
| Aristoflex AVC | (Ammonium acryloyldimethyltaurate/VP) copolymer | x | |
| Aristoflex Velvet | Polyacrylate crosspolymer-11 | x | |
| SENSOMER 10M | Polyquaternium-10 | x | |
| Rhaball Gum CG-M | Guar hydroxypropyltrimonium chloride | x | |
| HEC SE600 | Hydroxyethyl cellulose | x | |
| AEROSIL 200 | Silica | ○ | |
| OLEOCRAFT HP-31-PA-(MV) | Polyamide-3 | x | Oil thickener |
| Rheopearl TT2 | (Palmitate/ethylhexanoate) dextrin | x | |
| Rheopearl KL2 | Dextrin palmitate | x | |
| Rheopearl TL2 | Dextrin palmitate | x | |
| Rheopearl MKL2 | Dextrin myristate | x | |
| Rheopearl ISK2 | Stearoyl inulin | x | |
| Rheopearl ISL2 | Stearoyl inulin | x | |
| BENTONE GEL ISDV | Isododecane, disteardimonium hectorite, propylene carbonate | x | |
| Rheopearl WX | (Palmitate/hexyldecanoate) dextrin | x | |

<Temperature-increasing Test of Warming Compositions>

Figure 5:
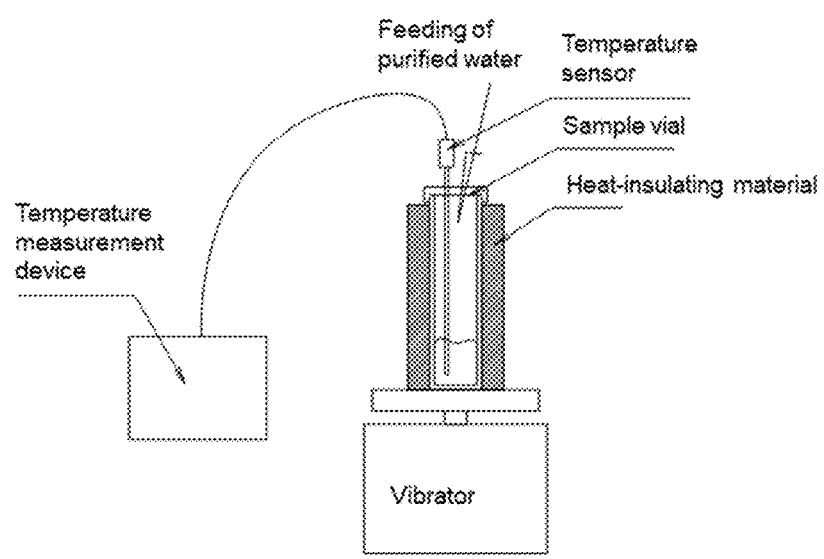
FIG. 5 is a schematic diagram of a device for measuring an increase in the temperature of a warming composition with time.
Figure 6:
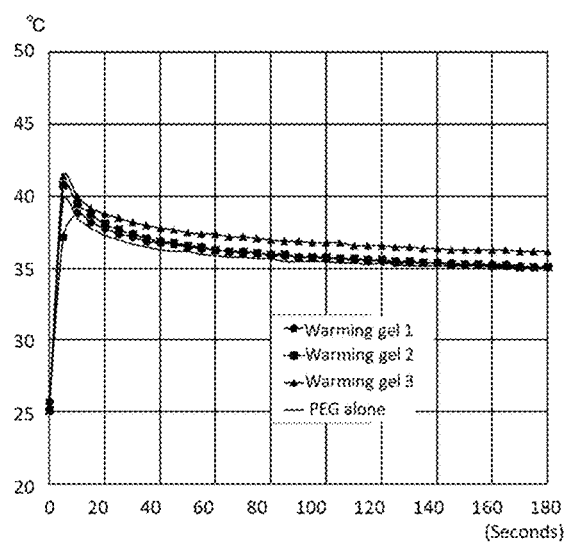
FIG. 6 is a graph showing an increase in the temperature of a warming composition according to one embodiment of the present invention with time.
Figure 6:
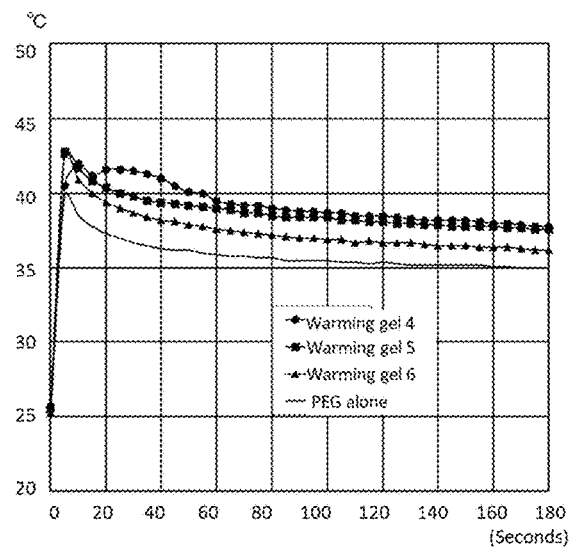

The components shown in Table 3 were mixed together to produce warming gels 1 to 15. A temperature-increasing test was carried out using a measurement device shown in FIG. 5 with an ambient temperature setting of about 25° C. Each of the warming gels 1 to 15 was taken in an amount of 5 cc, and placed in a sample vial, followed by incubation with a heat-insulating material. After insertion of a temperature sensor, a vibrator was operated to start temperature measurement using a thermocouple. The measurement was carried out at 5-second intervals. To the sample vial, 5 cc of purified water was fed. While the resulting mixture was stirred with the vibrator, changes with time in the temperature caused by the mixing of the warming gel with the purified water were measured. The results for the warming gels 1 to 6 are shown in FIG. 6. It can be seen that the warming compositions containing zeolite nanoparticles can produce warmth equivalent to that of the products containing zeolite micron particles. Although the results are not shown, the warming gels 7 to 15 also produced warmth equivalent to that of the products containing zeolite micron particles.

TABLE 3

| | Warming gel No. | | | | | | | | | | | | | | | |
|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | PEG alone |
| Zeolite nanoparticles (50 nm) | 9.1 | | | 16.7 | | | 23.1 | | | 28.6 | | | 33.3 | | | |
| Zeolite nanoparticles (300 nm) | | 9.1 | | | 16.7 | | | 23.1 | | | 28.6 | | | 33.3 | | |
| Zeolite micron particles (15 μm) | | | 9.1 | | | 16.7 | | | 23.1 | | | 28.6 | | | 33.3 | |
| PEG 400 | 88.2 | 88.2 | 88.2 | 80.8 | 80.8 | 80.8 | 74.6 | 74.6 | 74.6 | 69.3 | 69.3 | 69.3 | 64.7 | 64.7 | 64.7 | 97.0 |
| AEROSIL 200 | 2.7 | 2.7 | 2.7 | 2.5 | 2.5 | 2.5 | 2.3 | 2.3 | 2.3 | 2.1 | 2.1 | 2.1 | 2.0 | 2.0 | 2.0 | 3.0 |
| Total | 100.0 | 100.0 | 100.0 | 100.0 | 100.0 | 100.0 | 100.0 | 100.0 | 100.0 | 100.0 | 100.0 | 100.0 | 100.0 | 100.0 | 100.0 | 100.0 |

<Test for Evaluating Feeling of Use of Warming Compositions>

Instead of PEG, which was used in Example 2, 69.2% by mass glycerin was used to prepare a warming composition of Example 5. Together with Example 2 and Comparative Example 2, the composition of Example 5 was evaluated for physical properties after mixing with water. Example 2 showed an improved feeling of use because of its increased viscosity after mixing with water. On the other hand, Comparative Example 2 showed no increase in the viscosity after mixing with water, and exhibited a zeolite-specific feeling (rough feeling). Example 5 showed no change in the viscosity after mixing with water, but exhibited a sufficient feeling for application to the skin of a human body.

<Test of Storage Stability of Aerosol Formulations>

An aerosol formulation in which Example 1 as a first composition and an aqueous gel as a second composition were filled (Example 6), and an aerosol formulation which is the same as Example 6 except that Comparative Example 1 was used as the first composition (Comparative Example 3), were stored at room temperature in an upright position or an inverted position. At 1-week intervals, each aerosol formulation was sprayed for about 1 second to evaluate clogging, leakage, and abnormality of the mixed composition of the first and second compositions.

As a result, in Example 6, in either the case of storage in an upright position or the case of storage in an inverted position, there was neither clogging nor leakage, and a mixed composition with a favorable feeling could be prepared, even at Week 12. In contrast, in Comparative Example 3, clogging occurred at Week 2 in the product stored in an inverted position. Further, although the product stored in an upright position showed neither clogging nor leakage even at Week 12, precipitation of the powder contained in the first composition occurred at Week 1, so that sufficient warmth for application to the skin of a human body could not be obtained.

According to the present invention, a warming composition having a high warming impact during use can be provided. Further, in the aerosol formulation containing the warming composition of the present invention, neither the first composition nor the second composition is exposed to the air outside the container. Thus, absorption of moisture by zeolite, which is hygroscopic in general, can be prevented, and unexpected production of a heat-generating action does not occur, so that long-term storage stability can be obtained. Further, use of zeolite nanoparticles having a small average particle size enables production of a warming composition in which a favorable feeling of use can be achieved because of the absence of rough feeling, and in which an excellent storage stability can be achieved because of improved dispersion stability.

Although the present invention has been described with reference to specific embodiments, each embodiment was presented as an example and does not limit the scope of the present invention. Each of the embodiments described herein can be variously modified without departing from the spirit of the invention, and can be combined with characteristics described by other embodiments so long as it can be enabled.

DESCRIPTION OF SYMBOLS

100, 200, 300 Aerosol formulation
1 First container
11a First inner container
11b First outer container
2 Second container
12a Second inner container
12b Second outer container
3, 13, 23 Space
4 Housing
5, 15, 25 Discharge mechanism
16 Cap

What is claimed is:

1. A warming composition comprising zeolite nanoparticles having an average particle size of 20 nm to 500 nm, a polyhydric alcohol, and a thickener or a dispersant, wherein the polyhydric alcohol is polyethylene glycol, and the thickener or dispersant is fumed silica.

2. The warming composition according to claim 1, wherein the warming composition is a gel formulation or a cream formulation.

3. An aerosol formulation comprising: a first container containing a first composition containing at least the composition according to claim 1; and a second container containing a second composition containing at least water; the first container and the second container being contained in a discharge container provided with a discharge mechanism, wherein a space formed between the discharge container and the first container and the second container is filled with a propellant.

4. An aerosol formulation comprising a first container containing a first composition containing at least the composition according to claim 1, the first container being contained in a discharge container provided with a discharge mechanism, wherein a space formed between the first container and a partition wall of the discharge container in the discharge container is filled with a propellant.

5. The aerosol formulation according to claim 3, wherein the discharge mechanism allows simultaneous discharge of a filling in the first container and a filling in the second container.

6. An aerosol formulation comprising: a first container filled with a first composition containing at least the composition according to claim 1; and a second container filled with a second composition containing at least water; the first container and the second container being contained in a discharge container provided with a discharge mechanism, wherein a space formed between the discharge container and the first container and the second container is filled with a propellant, wherein the first composition and the second composition contact each other to generate heat when the compositions are discharged by the propellant.

7. A method for providing warming for a human body, the method comprising the steps of:
preparing the composition according to claim 1; and
applying the composition to the human body.

8. The warming composition according to claim 1, wherein the zeolite nanoparticles have an average particle size of 20 nm to 300 nm.

9. The warming composition according to claim 1, wherein the content of the zeolite nanoparticles is 1% by mass to 70% by mass with respect to 100% by mass of the warming composition.

10. The warming composition according to claim 1, wherein the viscosity of the warming composition is 1 mPa·s to 100,000 mPa·s.

11. The warming composition according to claim 1, wherein the content of the thickener or the dispersant is 0.01% by mass to 20% by mass with respect to 100% by mass of the warming composition.

\* \* \* \* \*